United States Patent
Al Hasan et al.

(10) Patent No.: US 11,288,296 B2
(45) Date of Patent: Mar. 29, 2022

(54) DEVICE, SYSTEM, AND METHOD FOR DETERMINING INFORMATION RELEVANT TO A CLINICIAN

(71) Applicant: KONINKLIJKE PHILIPS N.V., Eindhoven (NL)

(72) Inventors: Sheikh Sadid Al Hasan, Cambridge, MA (US); Oladimeji Feyisetan Farri, Yorktown Heights, NY (US); Junyi Liu, Windham, NH (US); Yuan Ling, Somerville, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 182 days.

(21) Appl. No.: 15/764,408

(22) PCT Filed: Sep. 28, 2016

(86) PCT No.: PCT/IB2016/055786
§ 371 (c)(1),
(2) Date: Mar. 29, 2018

(87) PCT Pub. No.: WO2017/060795
PCT Pub. Date: Apr. 13, 2017

(65) Prior Publication Data
US 2018/0307749 A1    Oct. 25, 2018

Related U.S. Application Data

(60) Provisional application No. 62/238,412, filed on Oct. 7, 2015.

(51) Int. Cl.
*G06F 16/335* (2019.01)
*G06F 16/31* (2019.01)
(Continued)

(52) U.S. Cl.
CPC .......... *G06F 16/337* (2019.01); *G06F 16/313* (2019.01); *G06F 16/335* (2019.01);
(Continued)

(58) Field of Classification Search
CPC .................................................... G06F 16/337
See application file for complete search history.

(56) References Cited

U.S. PATENT DOCUMENTS

| 2005/0198056 A1* | 9/2005 | Dumais ............... G06F 16/9535 |
| 2008/0016020 A1* | 1/2008 | Estes ..................... G16H 50/70 |
| | | 706/52 |

(Continued)

FOREIGN PATENT DOCUMENTS

WO        2012015958 A2    2/2012

OTHER PUBLICATIONS

Faensen, et al., "Hermes—A Notification Service for Digital Libraries", Proceedings of the 1st ACM/IEEE-CS Joint Conference on Digital Libraries, Roanoke Virginia, Jan. 31, 2001, pp. 373-380.
(Continued)

*Primary Examiner* — Van H Oberly

(57) ABSTRACT

A system, method and device for determining and notifying a clinician of information relevant to the clinician. The method that is performed by the device or system includes identifying at least one keyword in a user profile of a clinician, identifying at least one content word in a new information item, determining a relevance score between the new information item and the clinician based on the at least one keyword and the at least one content word and when the relevance score is above a predetermined threshold value, generating a notification for the clinician indicating the new information item.

20 Claims, 3 Drawing Sheets

(51) Int. Cl.
*G06F 16/951* (2019.01)
*G06F 16/332* (2019.01)
*G16H 15/00* (2018.01)

(52) U.S. Cl.
CPC ........ *G06F 16/3329* (2019.01); *G06F 16/951* (2019.01); *G16H 15/00* (2018.01)

(56) References Cited

U.S. PATENT DOCUMENTS

| | | | |
|---|---|---|---|
| 2009/0216563 A1* | 8/2009 | Sandoval | G06F 16/9535 705/3 |
| 2014/0046976 A1 | 2/2014 | Zhang et al. | |
| 2015/0046435 A1* | 2/2015 | Donneau-Golencer | G06F 16/24578 707/722 |
| 2015/0066922 A1 | 3/2015 | Xiong et al. | |
| 2016/0371271 A1* | 12/2016 | Bhatia | G06F 16/9535 |

OTHER PUBLICATIONS

Bollacker, et al., "CiteSeer: An Autonomous Web Agent for Automatic Retrieval and Identification of Interesting Publications", Proceedings of the 2nd International Conference on Autonomous Agents, Minneapolis/St. Paul, MN, May 9-13, 1998, pp. 116-123.

\* cited by examiner

DEVICE, SYSTEM, AND METHOD FOR DETERMINING INFORMATION RELEVANT TO A CLINICIAN

CROSS-REFERENCE TO PRIOR APPLICATIONS

This application is the U.S. National Phase application under 35 U.S.C. § 371 of International Application No. PCT/IB2016/055786, filed on Sep. 28, 2016, which claims the benefit of U.S. Provisional Application Ser. No. 62/238,412, filed Oct. 7, 2015. These applications are hereby incorporated by reference herein, for all purposes.

BACKGROUND INFORMATION

A clinician may provide healthcare or health-related information to patients in person or through communications such as online communications. Even with the knowledge that the clinician may be skilled in a concentrated medical field, the clinician may still refer to external sources to aid in determining the proper healthcare or health-related information to provide to the patient. The clinician may be limited (particularly in efficiency) in utilizing available information.

Clinicians are interested in specific information and/or knowledge about their own scientific domain or related specialties. With an ever increasing amount of available information (e.g., digital information), a clinician may find the process of manually tracking all available information sources and manually mining these sources to retrieve desired information, particularly in real-time, to have access to the most up-to-date knowledge to be extremely time consuming or nearly impossible. For example, if a clinician is interested in how a medical colleague treats patients with similar disease manifestations, the clinician would have to manually browse through the electronic medical records (EMR) for relevant medical reports or personally contact other clinicians to update the clinician's knowledge. In another example, to be acquainted with the most up-to-date knowledge outside the EMR, clinicians would have to manually sift through large volumes of available information sources to extract the relevant content of interest. This process is tedious and prone to errors because important information is missed by the clinicians leading to increased risk for medical errors and compromised patient safety.

Furthermore, the manual approach to searching information also leads to long time delays in retrieving clinically relevant information which may adversely affect efficient delivery of high quality care to patients. For example, if there is a sudden emergence of an infectious disease or a recent discovery of a critical clinical practice method, a clinician wants to have this information to optimize any clinical decision making process.

SUMMARY

The exemplary embodiments are related to a method for determining and notifying a clinician of information relevant to the clinician. The method includes identifying at least one keyword in a user profile of a clinician, identifying at least one content word in a new information item, determining a relevance score between the new information item and the clinician based on the at least one keyword and the at least one content word and when the relevance score is above a predetermined threshold value, generating a notification for the clinician indicating the new information item.

The exemplary embodiments are also related to a relevance server that has a transceiver communicating via a communications network, the transceiver configured to receive clinician information and a new information item and a memory storing an executable program. The relevance server also has a processor that executes the executable program which causes the processor to perform operations including identifying at least one keyword in a user profile of a clinician, identifying at least one content word in a new information item, determining a relevance score between the new information item and the clinician based on the at least one keyword and the at least one content word, and when the relevance score is above a predetermined threshold value, generating a notification for the clinician indicating the new information item.

The exemplary embodiments are also related to a further method for determining and notifying a clinician of information relevant to the clinician. The further method includes receiving clinician information associated with a clinician, analyzing the clinician information to identify at least one keyword to generate a user profile for the clinician, monitoring information sources for a new information item, when the new information item is detected, analyzing the new information item to identify at least one content word in the new information item, determining a relevance score between the new information item and the clinician based on the at least one keyword and the at least one content word and generating a notification for the clinician indicating the new information item and a relevance factor of the new information item based on the relevance score.

DETAILED DESCRIPTION

Figure 1:
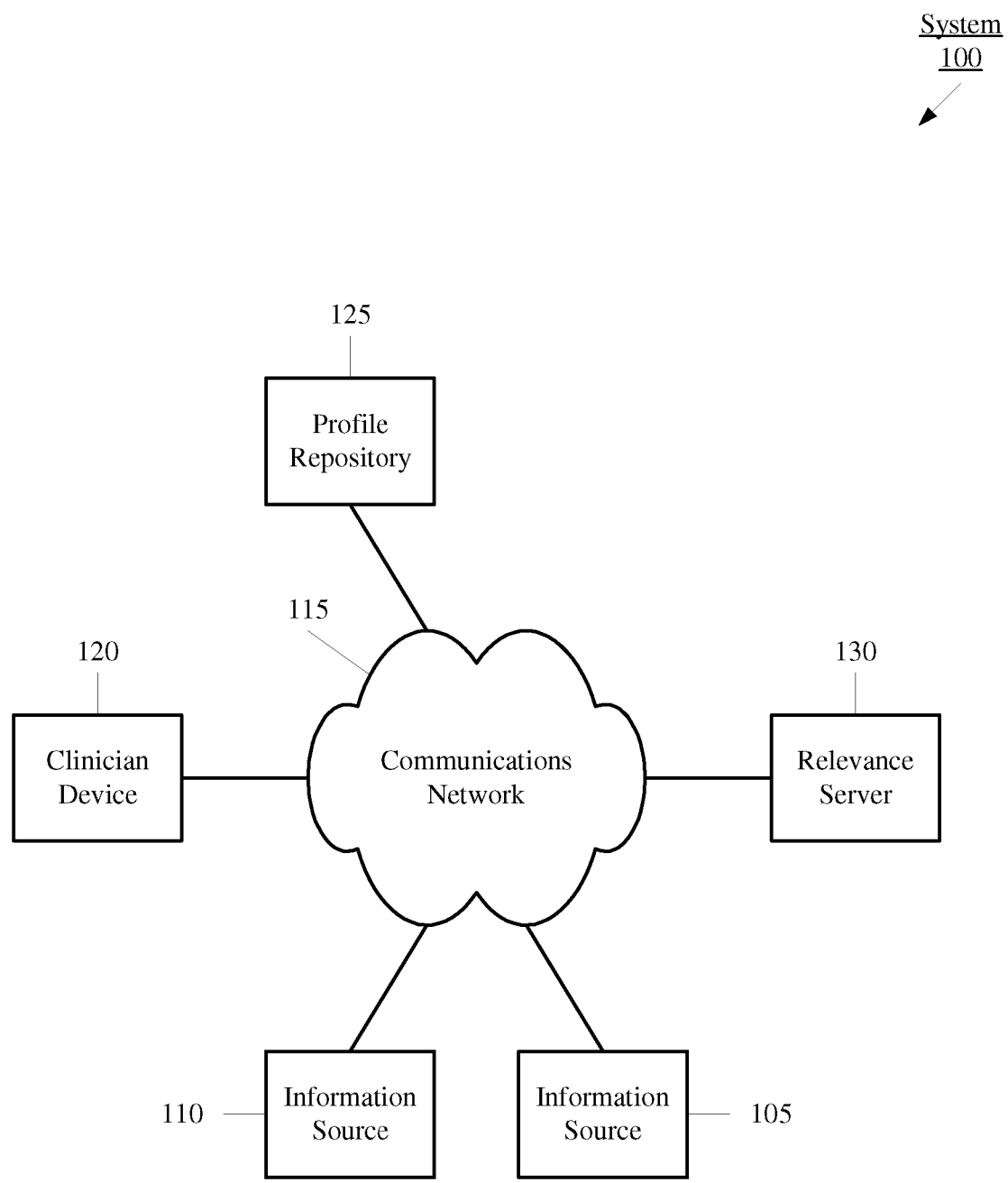
FIG. 1 shows a system according to the exemplary embodiments.

The exemplary embodiments may be further understood with reference to the following description and the related appended drawings, wherein like elements are provided with the same reference numerals. The exemplary embodiments are related to a device, a system, and a method for clinicians to provide a more efficient manner of care to patients by determining new available information that is relevant to a clinician. The exemplary embodiments are configured to automatically monitor information sources in real-time that are filtered to determine the most relevant content for a select clinician such that the clinician is notified of relevant content to make better-informed clinical decisions and improve healthcare quality and patient outcomes.

The exemplary embodiments minimize a time and an effort required by a clinician to manually review large volumes of clinical and biomedical information sources for specific clinical information/knowledge that potentially enhances clinical acumen and ensure better outcomes for their patients. Accordingly, the exemplary embodiments are configured to automatically monitor the available information streams in real-time, filter the most relevant content based on the interest profiles of the clinician, and deliver the content to the clinician promptly in a seamless and workflow-centric manner."

FIG. 1 shows a system 100 according to the exemplary embodiments. The system 100 relates to a communication between various components involved in providing healthcare and/or health-related information to a patient or user from a clinician. Specifically, the system 100 may include a plurality of information sources 105, 110, a communications network 115, a clinician device 120, a profile repository 125, and a relevance server 130. As will be described in further detail below, the system 100 is configured to utilize the information sources 105, 110 such that the healthcare and/or the health-related information may be provided using the first and/or second mechanism according to the exemplary embodiments.

The information sources 105, 110 may represent any source from which information is received. The information may be medical information, online or digital information, etc. For example, the information source 105 may include a repository for clinical reports in an electronic medical record (EMR). In another example, the information source 105 may include other medical-related data from medical journals, hospitals, etc. In a further example, the information source 110 may include online streams such as social media streams (e.g., a microblog website), health blogs, online news media, etc. For exemplary purposes, the information sources 105, 110 may provide any information that may be used in performing the first and second mechanisms according to the exemplary embodiments.

It should be noted that the system 100 illustrating two information sources 105, 110 is only exemplary. The information sources 105, 110 may represent one or more information sources that are configured to provide the information to the other components of the system 100. In fact, the information sources 105, 110 may represent each individual item that may be available from a repository or source, the repository or source itself, a collection of repositories, etc.

The communications network 115 may be configured to communicatively connect the various components of the system 100 to exchange data. The communications network 115 may represent any single or plurality of networks used by the components of the system 100 to communicate with one another. For example, if the relevance server 130 is used at an administration site, the communications network 115 may include a private network in which the relevance server 130 may initially connect (e.g. a hospital network). The private network may connect to a network of an Internet Service Provider to connect to the Internet. Subsequently, through the Internet, a connection may be established to other electronic devices. It should be noted that the communications network 115 and all networks that may be included therein may be any type of network. For example, the communications network 110 may be a local area network (LAN), a wide area network (WAN), a virtual LAN (VLAN), a WiFi network, a HotSpot, a cellular network (e.g., 3G, 4G, Long Term Evolution (LTE), etc.), a cloud network, a wired form of these networks, a wireless form of these networks, a combined wired/wireless form of these networks, etc.

The clinician device 120 may represent any electronic device that is configured to perform the functionalities associated with a clinician. For example, the clinician device 120 may be a portable device such as a tablet, a laptop, etc. or a stationary device such as a desktop terminal. The clinician device 120 may include the necessary hardware, software, and/or firmware to perform the various operations associated with medical treatment. The clinician device 120 may also include the required connectivity hardware, software, and firmware (e.g., transceiver) to establish a connection with the communications network 115 to further establish a connection with the other components of the system 100. For example, the clinician device 120 may schedule appointments for patients using a calendar application, may track treatments or procedures of a patient, etc. In another example, the clinician device 120 may be used to post online content such as microblogs. In a further example and as will be described in further detail below, the clinician device 120 may receive notifications from the relevance server 130 regarding new available information.

The profile repository 125 may be a component that stores user profiles. Specifically, the profile repository 125 may store user profiles of clinicians. As will be described in further detail below, the relevance server 130 may generate user profiles that may be stored in the profile repository 125. If the profile repository 125 already has a user profile for a particular clinician, the relevance server 130 may query the profile repository 125 to retrieve the corresponding user profile.

Figure 2:
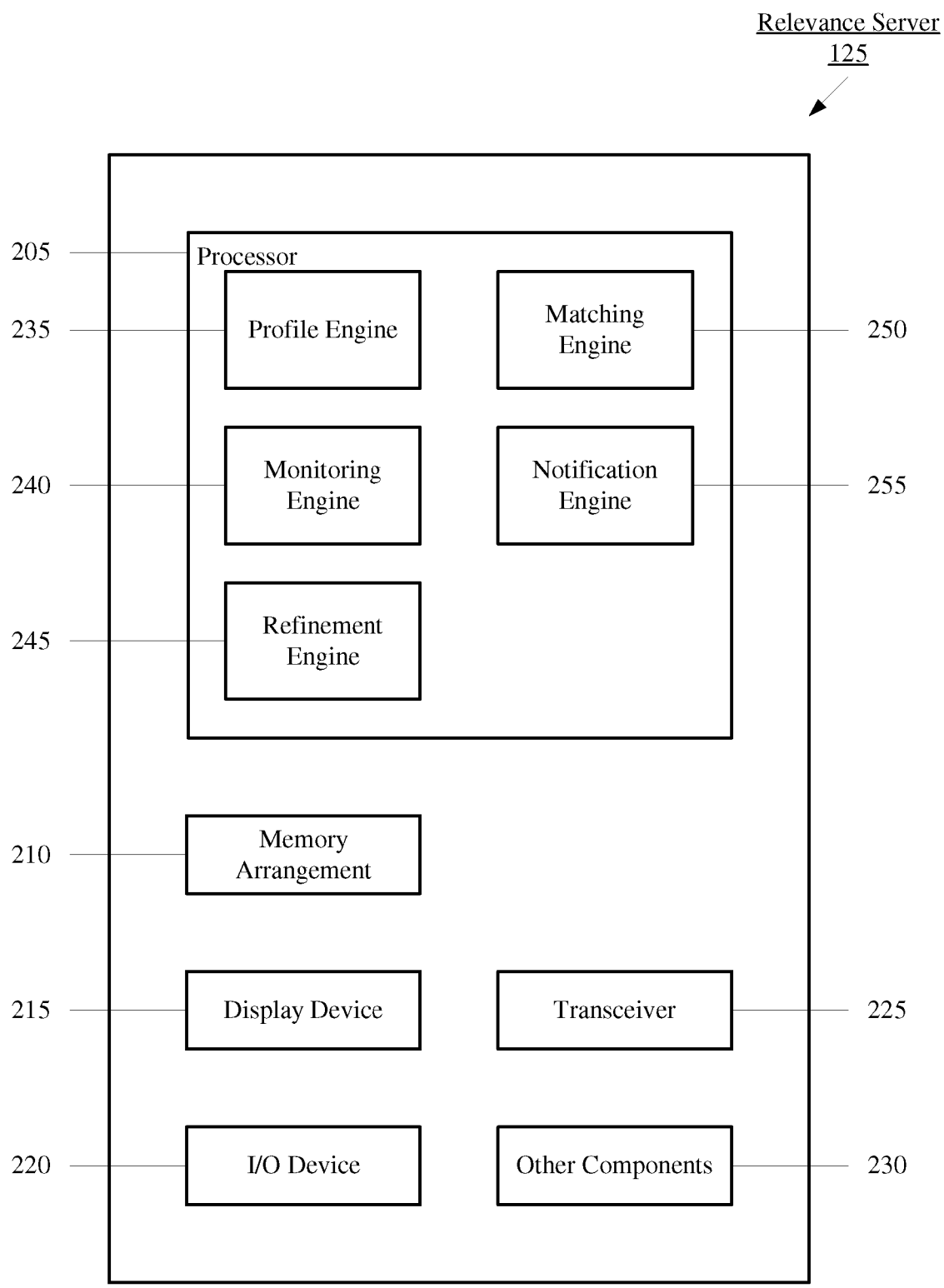
FIG. 2 shows a relevance server of FIG. 1 according to the exemplary embodiments.

The relevance server 130 may be a component of the system 100 that performs functionalities associated with the first mechanism of the exemplary embodiments. FIG. 2 shows the relevance server 130 of FIG. 1 according to the exemplary embodiments. The relevance server 130 may provide various functionalities in determining relevant new available information and notifying a clinician of these relevant new available information. Although the relevance server 130 is described as a network component (specifically a server), the relevance server 130 may be embodied in a variety of hardware components such as a portable device (e.g., a tablet, a smartphone, a laptop, etc.), a stationary device (e.g., a desktop terminal), incorporated into the personal device such as a physician device, incorporated into a website service, etc. The relevance server 139 may include a processor 205, a memory arrangement 210, a display device 215, an input and output (I/O) device 220, a transceiver 225, and other components 230 (e.g., an imager, an audio I/O device, a battery, a data acquisition device, ports to electrically connect the reporting server 130 to other electronic devices, etc.).

The processor 205 may be configured to execute a plurality of applications of the relevance server 130. As will be described in further detail below, the processor 205 may utilize a plurality of engines including a profile engine 235, a monitoring engine 240, a refinement engine 245, a matching engine 250, and a notification engine 255. The profile engine 235 may analyze interest profiles of a clinician to determine an overall context of information needs through generation of a user profile of the clinician. The monitoring engine 240 may monitor the information sources 105, 110 in real-time to track any new available information. The refinement engine 245 may process the results of the monitoring engine 240 to refine the results. The matching engine 250 may determine select ones of the refined results based on the user profile of the clinician. The notification engine 255 may generate notifications for the clinician of the select ones of the refined results.

It should be noted that the above noted applications and engines each being an application (e.g., a program) executed by the processor 205 is only exemplary. The functionality associated with the applications may also be represented as components of one or more multifunctional programs, a separate incorporated component of the relevance server 130 or may be a modular component coupled to the relevance server 130, e.g., an integrated circuit with or without firmware.

The memory 210 may be a hardware component configured to store data related to operations performed by the relevance server 130. Specifically, the memory 210 may store data related to the various engines 235-255 such as the user profile of the clinician and the data from the information sources 105, 110. The display device 215 may be a hardware component configured to show data to a user while the I/O device 220 may be a hardware component that enables the user to enter inputs. For example, an administrator of the relevance server 130 may maintain and update the functionalities of the relevance server 130 through user interfaces shown on the display device 215 with inputs entered with the I/O device 220. It should be noted that the display device 215 and the I/O device 220 may be separate components or integrated together such as a touchscreen. The transceiver 225 may be a hardware component configured to transmit and/or receive data via the communications network 110.

According to the exemplary embodiments, the relevance server 130 may perform various different operations to determine which of the newly available information is related to a particular clinician. Initially, as described above, the profile engine 235 may analyze interest profiles of a clinician to determine an overall context of information needs through generation of a user profile of the clinician. The profile engine 235 may provide an initial operation in which profile information is gathered to determine the user profile of a particular clinician. The profile information related to the user profile that may be gathered may be of any type and received from the information sources 105, 110 or manually from the clinician. For example, the profile information may include a resume of the clinician, expertise profiles saved in various depositories (e.g., a hospital management system), information collected via a short interactive online survey of the specific information needs of the clinician, etc.

The profile application 235 may be configured to analyze the profile information. For example, the profile application 235 may utilize a topic modelling/topic signature operation to extract topical keywords that capture the overall context of the interest profile of the clinician. The topic modelling operation may tend to discover abstract topics from a collection of datasets through statistical analyses of words across documents. The topic signature operation may identify a word as a topical word if the word has significantly greater probability in a given text compared to a large background corpus. The extracted topical keywords along with various possible n-gram combinations may be utilized to expand the topical vocabulary by extracting related synonym sets from an open source lexical database (e.g., WordNet) and via exploiting deep neural word/phrase embeddings. The neural word/phrase embeddings may be trained from a large collection of data garnered from various online information sources by using a deep learning-based word/phrase to vector representation modelling operation. In this framework, each word/phrase may be mapped to a unique vector using a skip-gram model architecture. Once the training converges, words/phrases with similar meanings may be co-located in the vector space such that the position and/or difference in positions may be exploited to determine a relatedness among different words/phrases. The expanded topical keyword list per user profile may be stored via a text indexing application for further analyses during real-time information content filtering, to be described in further detail below. In this manner, the profile application 235 may generate a user profile of the clinician including various keywords associated with the clinician.

The monitoring engine 240 may monitor the information sources 105, 119 in real-time to track any new available information. The monitoring engine 240 may monitor various online and/or other information streams included in the information sources 105, 110. For example, the information streams may include social media data such as Twitter, blog posts, online news media, EMR free text medical reports, etc. that are tracked in real-time to determine any incoming new posts and/or reports.

The refinement engine 245 may process the results of the monitoring engine 240 by refining the results. Specifically, the refinement engine 245 may process incoming information, perform a tokenization operation and/or a parts-of-speech (POS) tagging operation, and remove noisy elements to generate a "clean" version of the new available information identified by the monitoring engine 240. It is noted that the information being monitored by the monitoring engine 240 may be streamed in various formats. For example, the information may be streamed as short sentences (e.g., tweets from Twitter), as a collection of one or more paragraphs (e.g., status posts from social media sites, blog posts, etc.), as documents and/or reports (e.g., from the EMR), etc. When new available information is received by the monitoring engine 240, the refinement engine 245 may process the new available information to remove all possible noise depending on the information source and based on the format that the information is streamed. Specifically, noisy content is removed using rule-based operations corresponding to the streamed format in association with curated knowledge databases about domain-dependent noisy words/templates. The refinement engine 245 may apply natural language processing (NLP) operations such as tokenization and POS tagging towards extracting important content words that preserves the contextual meaning of the content of the streamed information. In this manner, the clean version of the new available information including content words of the new available information may be generated.

The matching engine 250 may determine select ones of the refined results that are appropriate for the clinician based on the user profile of the clinician. Specifically, the matching engine 250 may use NLP operations and information retrieval techniques to analyze the clean version of the new available information with respect to the user profile of the clinician to determine appropriate matches. The matching engine 250 may utilize the content words from the refinement engine 245 as a query that are matched with the keywords of the user profile of the clinician (e.g., by using a text indexing operation). The text indexing operation may utilize the content words as various combinations of possible n-grams/phrases to find an overall content match across the keywords of the user profile.

The relevance of an item in the new available information to the user profile of the clinician may be measured in a two step process. In a first step, the text indexing operation may return a term frequency-inverse document frequency (TF-IDF) based content matching score with respect to the user profile of the clinician. Specifically, a text indexing score may be generated. In a second step, the keywords from the user profile may be further utilized to determine a semantic similarity with the content words of the new available content through a semantic similarity measurement operation built on semantic networks of related words and corpus-based statistics. Specifically, a semantic similarity score may be generated.

The matching engine 245 may utilize weighting factors that are associated with the text indexing score and the semantic similarity score. The weighting factors may provide a dynamic approach to utilize the text indexing score and the semantic similarity score where a greater indexing or a greater similarity may allow the corresponding score to be weighted accordingly and provide a more significant factor. Thus, the matching engine 245 may combine the text indexing score weighted by its weighting factor and the semantic similarity score weighted by its weighting factor to generate an overall relevance score of the new available information item to the user profile of the clinician. The overall relevance score may be indicative of how relevant the new available information item is for a particular clinician. Thus, a first new available information item having a first overall relevance score may be greater than a second overall relevance score of a second new available information item. Accordingly, the first new available information item may have a higher relevance to the clinician. The matching engine 245 may also determine a semantic similarity of a new available information item with other new available information items that may have already been communicated to the clinician. This operation may provide a redundancy check such that the clinician is not overwhelmed by repeated information.

The notification engine 255 may generate notifications for the clinician of the select ones of the refined results. Specifically, the notification engine 255 may transmit content notifications to a clinician when new available information items are identified as relevant (e.g., corresponding to the information of the user profile of the clinician). For example, if the overall relevance score of a new available information item is greater than a predetermined threshold value (e.g., determined empirically after sufficient amount of training), the new available information item may be transmitted to the clinician. For example, the notification engine 255 may generate a corresponding message that is transmitted (e.g., mobile push notification in real-time, email, etc.). In this manner, the clinician may be aware of interesting new available information as soon as it becomes available (e.g., within a few seconds of the new available information becoming available).

The notification engine 250 may be configured to generate the notifications in a variety of different manners. In a first example, a generic message may be generated to indicate that new available information items have been detected. In another example, a more specific message may be generated that includes links or other pointers that lead the clinician to the new available information item. In a further example, a descriptive message may be generated in which a most relevant sentence or passage is included in the message regarding the new available information item such that the clinician may read the provided text and determine whether to proceed further. The descriptive message may also utilize the more specific message feature of including links to easily allow the clinician to proceed.

The notification engine 250 may also be configured to be modified, particularly to limit the number of notifications over a period of time. In this manner, the clinician may not be inundated with all new available information items. In a first example, the number of notifications to be delivered may be controlled by setting an upper limit (e.g., only 15 notifications per day). In a second example, the time that notifications are delivered may be customized such as based on the work schedule of the clinician so that notifications are not delivered during an unwanted time period (e.g., when the clinician is doing rounds, in surgery, or asleep). In a third example, the clinician may utilize a personalized predetermined threshold value so that more relevant items (e.g., a higher value than the machine-learned value) or less relevant items (e.g., a lower value than the machine-learned value) may be included in the notification. In a fourth example, the notifications may be bundled such that new available information items are stored and later analyzed such that the top new available information items having at least a particular overall relevance score are included in a message to be delivered (e.g., email). The timing of this process may be an extended time period (e.g., once per day, once per week, etc.).

In a specific implementation of the relevance server 130, results of new available information items may be determined based on various clinical questions to be satisfied. For example, a primary use case may relate to a scenario where a clinician may seek relevant research-based evidence on how best to care for patients at the point of care. Specifically, the clinician may require specific information on the patient's most likely diagnosis given a list of signs/symptoms, the most essential tests/procedures in a given scenario, and the most effective treatment plan given a diagnosis. Accordingly, the exemplary embodiments are configured with an objective of retrieving a ranked list of results that answer questions related to multiple categories of clinical information needs. In a particular example, short medical case reports are associated with one of three generic clinical questions: "What is the patient's diagnosis?", "What tests should the patient receive?", and "How should the patient be treated?". The results may be judged in terms of their relevance to the corresponding clinical question. This may relate particularly to the monitoring engine 240 and the refinement engine 245.

As described above, the exemplary embodiments provide a NLP-driven method that combines syntactic, semantic, and filtering operations towards extracting relevant biomedical articles corresponding to clinical concepts (e.g., diagnoses, treatment, and/or tests) relevant to each given topic. This particular implementation may also utilize the above engines such as (i) the topical analysis of identifying the most relevant content words from the information sources 105, 110, (ii) the clinical inferencing where reasoning through the content words arrive at the diagnoses, tests, and treatments based on underlying clinical contexts by using neural phrase embeddings and/or an external clinical knowledge base, and (iii) relevant article retrieval where retrieving and ranking pertinent biomedical articles based on the content words and clinical inferences from (i) and (ii).

In the topical analysis, the TF-IDF described above may be utilized from given descriptions and/or summaries and mapped to categories represented in controlled clinical vocabularies and/or ontologies. The TF-IDF may also be identified relevant to demographic information, interpreted vital patient parameters based on standard normal range values, and filtered out negated clinical concepts to give more weight to positive clinical manifestations in a given patient scenario. Those skilled in the art will appreciate that the use of clinical domain ontologies may be particularly effective as they have been implemented to promote standard clinical vocabulary and are widely used to semantically categorize clinical concepts, and facilitate information exchange and interoperability.

In the clinical inferencing, a word/phrase-to-vector neural phrase embedding model is used (which has been trained on over 4 million clinically relevant sentences garnered from multiple clinical data sources, articles, and discharge summaries) to capture the overall context of a given topic description or summary towards inferring the differential diagnoses based on the commonest clinical diagnoses represented in clusters of identified topical content words from the topical analysis step. A skip-gram model architecture may be utilized to learn vector representations of words and phrases as reported to provide improved results. The list of possible diagnoses may be further validated, filtered, and ranked by referencing a clinical knowledge base which is indexed, and a list of candidate articles with relevant diagnoses corresponding to each topical content word may be extracted. Through this process, relationships between topical content words and associated clinical concepts (e.g., diagnoses/disorders, treatment, and test) may be found within a comprehensive knowledge base for the purpose of biomedical evidence retrieval.

In the relevant article retrieval, topical content words and the corresponding disorders/diagnoses, tests, and treatments obtained from the clinical inferencing operation may be used to retrieve candidate biomedical articles by searching through abstracts of given articles. Candidate results may be ranked using multiple weighting operations designed to address the three types of clinical questions (e.g., diagnosis, test, and treatment). The retrieved results may be further filtered by location, demographic information, and other contextual information from the topic description/summary towards improving a relevance of the results. The final list may further be ordered by publication date of the new available information items to provide a chronological biomedical evidence for the answers to each topic.

In performing the above implementation of the relevance server 130 according to the exemplary embodiments, an experimental set of data may be used. For example, a test dataset may include thirty topics divided into three question types such as those described above. The given topic descriptions or topics may be essentially medical case narratives that describe scenarios related to patient medical history, signs/symptoms, diagnoses, tests, and treatments. The topics may be provided in two versions depending on the depth of information. Topic descriptions may include comprehensive descriptions of the patient situation whereas topic summaries may contain the most important information. Furthermore, ground truth diagnoses may be provided for the test and treatment topics.

Running an experiment with the above datasets, an evaluation may be conducted using standard evaluation procedures (e.g., Text Retrieval Conference (TREC) procedures) for ad hoc information retrieval tasks. The highest ranked biomedical articles may be sampled and judged by medical domain experts on a three-point scale of 0 (not relevant), 1 (possibly relevant), and 2 (definitely relevant) depending on the relevance of the answer to the associated question type about a given scenario. The results indicate that the clinical question answering system according to this implementation of the exemplary embodiments perform close to median scores for all evaluation measures. Analysis of the results also demonstrate that the clinical question answering system according to the exemplary embodiments may achieve better results for certain topics when topic summaries are used whereas neural word/phrase embeddings improve upon scores for a number of topics. The results also indicate that the identification and use of accurate differential diagnoses has a significant impact on the accuracy of the relevant biomedical article retrieval.

This implementation of the relevance server 130 according to the exemplary embodiments may also utilize a real-time filtering system, particularly of a microblog. Using the above engines, this particular implementation may (i) analyze user profiles that leverage neural word/phrase embeddings for contextual understanding, (ii) analyze microblog content where a noisy element filtering operation as well as a tokenization and POS tagging operation for generation of a cleaned version of the microblog are performed, and (iii) matching relevant content where mapping of relevant microblogs to a corresponding user profile is through a combination of a TF-IDF based content matching score and a semantic similarity score. This may relate particularly to the profile engine 235 and the matching engine 250.

In the analysis of user profiles, a plurality of different user profiles may be analyzed using a topic signature operation that extracts the most important keywords to capture the overall context of the information need. The keywords along with a corresponding n-gram combination may be utilized to expand the topical vocabulary by extracting related synonym sets and exploiting deep neural word/phrase embeddings. The neural word/phrase embeddings may be trained from over sixty million microblogs by using a deep learning-based word/phrase to vector representation modeling operation. The expanded keyword list per user profile may be indexed for further analyses during real-time microblog content filtering.

In the microblog content analysis, each incoming microblog may be processed to remove all noise using various rule-based operations in association with curated databases of known noisy elements that are widely used in microblogs. The tokenization and POS tagging may be applied to extract the most important words that preserve the contextual meaning of the microblog.

In the relevant content matching, the content words in the above described clinical question answering system and the keywords may be used as a query for which an appropriate user profile is retrieved and matched. The query may be transformed as various combinations of possible n-grams/phrases to determine an overall content match across the user profile. The final relevance therebetween may be measured using a weighted combination of two scores, the TF-IDF based content matching score and the semantic similarity score based on an operation built on semantic networks of related words and corpus-based statistics. Subsequently, the notification engine 255 may be used in notifying any matches.

Figure 3:
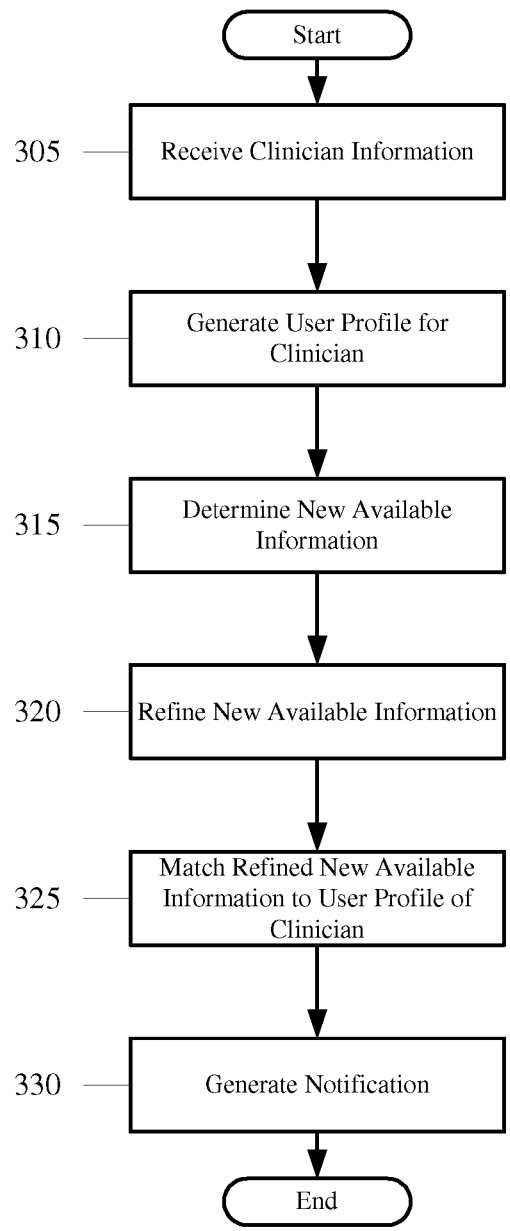
FIG. 3 shows a method for determining relevant new available information according to the exemplary embodiments.

FIG. 3 shows a method 300 for determining relevant new available information according to the exemplary embodiments. Specifically, the method 300 may relate to the mechanism of the exemplary embodiments in which a user profile is used to identify select ones of new available information items that are to be identified to a clinician associated with the user profile. Accordingly, the method 300 will be described from the perspective of the relevance server 130. The method 300 will also be described with regard to the system 100 of FIG. 1 and the plurality of engines 235-255 of the relevance server 130 of FIG. 2.

In step 305, the relevance server 130 via the profile engine 235 may receive information associated with a clinician. As described above, the information associated with the clinician may be received from the information sources 105, 110. For example, documentation of the clinician may be received such as a resume, an expertise profile, etc. In another example, the relevance server 130 may receive online data such as microblog information of the clinician. In step 310, the relevance server 130 via the profile engine 235 may generate a user profile for the clinician. Specifically, the information of the clinician may be analyzed to determine keywords that are included in the user profile.

In step 315, the relevance server 130 may determine new available information items. Specifically, the relevance server 130 via the monitoring engine 240 may monitor the information sources 105, 110 such as social media, blog posts, online news media, EMR free text medical reports, etc. The information sources 105, 110 may be updated periodically or dynamically by authors who add or post new available information. The relevance server 130 may be configured to identify the new available information items from a previous time.

In step 320, the relevance server 130 via the refinement engine 245 may refine the new available information. Specifically, the relevance server 130 may perform a tokenization operation and/or a POS tagging operation to remove noisy elements in the new available information items. The noisy elements may relate to portions of the new available information that is irrelevant to the features of the exemplary embodiments. The relevance server 130 may accordingly generate content words based on a clean version of the new available information items.

In step 325, the relevance server 130 via the matching engine 250 may match the content words of the new available information items with the keywords of the user profile of the clinician. Specifically, using NLP operations and information retrieval techniques, select ones of the new available information items may be identified as being relevant to the user profile of the clinician. Using a text indexing score with a corresponding weight and a semantic similarity score with a corresponding weight, an overall relevance score may be determined which indicates the relevance of a new available information item is to the user profile of the clinician. It is noted that new available information items that have no relevance may have a zero value whereas new available information items that have at least some relevance may have a positive value.

In step 330, the relevance engine 130 via the notification engine 255 may generate a notification for the clinician regarding any new available information items that have at least some relevance (positive overall relevance score). It is noted that the notification engine 255 may also utilize a predetermined threshold value as the basis of whether a new available information item is to be used in the notification (e.g., only if the overall relevance score of the new available information item is greater than the predetermined threshold value). The notification may be transmitted in a variety of different forms, at a variety of different times, using a variety of different factors, etc. The relevance engine 130 may also report any new available information item and include the overall relevance score to indicate how the new available information item relates to the user profile of the clinician.

The exemplary embodiments described above relate to clinicians and a medical field in which medical information is identified for the clinician. However, the use of the medical-related implementation is only exemplary. Those skilled in the art will understand that the exemplary embodiments may be modified accordingly to be used with any user profile and any document retrieval system based on the user profile.

The exemplary embodiments provide a device, system, and method of determining information relevant to a clinician. The exemplary embodiments provide a profile mechanism in which a user profile of a clinician is determined through a plurality of keywords. The exemplary embodiments provide an information mechanism in which new available information is identified and content words associated therewith are determined. The exemplary embodiments provide a matching mechanism in which a relevance of the new available information items are determined for the user profile of the clinician such that relevant new available information items are notified to the clinician.

Those skilled in the art will understand that the above-described exemplary embodiments may be implemented in any suitable software or hardware configuration or combination thereof. An exemplary hardware platform for implementing the exemplary embodiments may include, for example, an Intel x86 based platform with compatible operating system, a Windows platform, a Mac platform and MAC OS, a mobile device having an operating system such as iOS, Android, etc. In a further example, the exemplary embodiments of the above described method may be embodied as a computer program product containing lines of code stored on a computer readable storage medium that may be executed on a processor or microprocessor. The storage medium may be, for example, a local or remote data repository compatible or formatted for use with the above noted operating systems using any storage operation.

It will be apparent to those skilled in the art that various modifications may be made in the present disclosure, without departing from the spirit or the scope of the disclosure. Thus, it is intended that the present disclosure cover modifications and variations of this disclosure provided they come within the scope of the appended claims and their equivalent.

What is claimed is:

1. A method, comprising:
   at a relevance server:
   analyzing clinician information to extract at least one keyword to capture an overall context of at least one interest profile of a clinician;
   extracting, based on the extracted at least one keyword, at least one related synonym set from a lexical database;
   generating an expanded topical keyword list based on the extracted at least one related synonym set and at least one deep neural word/phrase embedding, the at least one deep neural word/phrase embedding trained from data based on words/phrases being mapped to unique vectors;
   storing the expanded topical keyword list via a text indexing application as a user profile for the clinician;
   in real time, monitoring information sources for a new information item;
   identifying at least one content word in the new information item that preserves the contextual meaning of the content of the new information item, wherein natural language processing operations including tokenization or parts-of-speech tagging are applied towards extracting the at least one content word;
   determining a relevance score between the new information item and the user profile of the clinician based on the at least one keyword and the at least one content word; and
   when the relevance score is above a personalized predetermined threshold value, generating a notification for the clinician indicating the new information item.

2. The method of claim 1, further comprising:
   receiving the clinician information associated with the clinician.

3. The method of claim 2, wherein the clinician information is based from at least one of a resume, available expertise profiles, surveys, and online content.

4. The method of claim 2, further comprising:
   identifying the at least one content word in the new information item when the new information item is detected; and generating the notification for the clinician indicating the new information item and a relevance factor of the new information item based on the relevance score.

5. The method of claim 1, wherein the information sources are based on at least one of social media data, blog posts, online news media, and electronic media records (EMR) reports.

6. The method of claim 1, wherein the at least one content word is refined by removing noisy content therein.

7. The method of claim 1, wherein the relevance score includes a text indexing score and a semantic similarity score.

8. The method of claim 7, wherein the text indexing score is based on a term frequency-inverse document frequency (TF-IDF) content matching operation, and wherein the semantic similarity score is based on semantic networks of related words and corpus-based statistics.

9. The method of claim 7, wherein the text indexing score is applied with a first weighting factor and the semantic similarity score is applied with a second weighting factor, and further comprising generating an overall relevance score based on the text indexing score, weighted by the first weighting factor, and the semantic similarity score, weighted by the second weighting factor.

10. The method of claim 1, further comprising:
transmitting the notification to the clinician based on at least one of a total number of notifications within a predetermined time period, a time of day, and a collection preference.

11. The method of claim 1, further comprising:
mapping the words/phrases to the unique vectors using a skip-gram model architecture.

12. The method of claim 1, further comprising:
determining an additional relevance score between the new information item provided to the clinician and an additional new information item from the information sources; and
when the additional relevance score is equal to or above a threshold value, withholding the additional new information item from the clinician to prevent the clinician from being overwhelmed by redundant information.

13. A relevance server, comprising:
a transceiver communicating via a communications network, the transceiver configured to receive clinician information and a new information item;
a memory storing an executable program; and
a processor that executes the executable program that causes the processor to perform operations, comprising,
analyzing the clinician information to extract at least one keyword to capture an overall context of at least one interest profile of a clinician;
extracting, based on the extracted at least one keyword, at least one related synonym set from a lexical database;
generating an expanded topical keyword list based on the extracted at least one related synonym set and at least one deep neural word/phrase embedding;
storing the expanded topical keyword list via a text indexing application as a user profile for the clinician;
in real time, monitoring information sources for the new information item;
identifying at least one content word in the new information item that preserves the contextual meaning of the content of the new information item wherein natural language processing operations including tokenization or parts-of-speech tagging are applied towards extracting the at least one content word;
determining a relevance score between the new information item and the user profile of the clinician based on the at least one keyword and the at least one content word, wherein the relevance score includes a text indexing score applied with a first weighting factor and a semantic similarity score applied with a second weighting factor;
generating an overall relevance score based on the text indexing score, weighted by the first weighting factor, and the semantic similarity score, weighted by the second weighting factor; and
when the relevance score is above a personalized predetermined threshold value, generating a notification for the clinician indicating the new information item.

14. The relevance server of claim 13, wherein the clinician information is based from at least one of a resume, available expertise profiles, surveys, and online content.

15. The relevance server of claim 13, wherein the operations further comprise monitoring information sources for the new information item and determining at least one first content word in the new information item, the at least one content word included in the at least one first content word.

16. The relevance server of claim 15, wherein the information sources are based on at least one of social media data, blog posts, online news media, and electronic media records (EMR) reports.

17. The relevance server of claim 15, wherein the at least one first content word is refined by removing noisy content therein.

18. The relevance server of claim 13, wherein the text indexing score is based on a term frequency-inverse document frequency (TF-IDF) content matching operation, and wherein the semantic similarity score is based on semantic networks of related words and corpus-based statistics.

19. A method, comprising:
at a relevance server:
receiving clinician information associated with a clinician;
analyzing the clinician information to extract at least one keyword to capture an overall context of at least one interest profile of the clinician;
extracting, based on the extracted at least one keyword, at least one related synonym set from a lexical database;
generating an expanded topical keyword list based on the extracted at least one related synonym set and at least one deep neural word/phrase embedding, the at least one deep neural word/phrase embedding trained from data based on words/phrases being mapped to unique vectors;
storing the expanded topical keyword list via a text indexing application as a user profile for the clinician;
monitoring, in real time, information sources for a new information item;
when the new information item is detected, analyzing the new information item to identify at least one content word in the new information item that preserves the contextual meaning of the content of the new information item, wherein natural language processing operations including tokenization or parts-of-speech tagging are applied towards extracting the at least one content word;

determining a relevance score between the new information item and the user profile of the clinician based on the at least one keyword and the at least one content word; and when the relevance score is above a personalized predetermined threshold value, generating a notification for the clinician indicating the new information item and a relevance factor of the new information item based on the relevance score.

20. The method of claim 19, wherein the words/phrases are mapped to the unique vectors using a skip-gram model architecture.

* * * * *